United States Patent [19]
Yamaguchi et al.

[11] Patent Number: 5,161,272
[45] Date of Patent: Nov. 10, 1992

[54] MATTRESS FOR MAGNETIC TREATMENT

[75] Inventors: Takayoshi Yamaguchi; Isamu Kobayashi, both of Tokyo, Japan

[73] Assignee: Japan Life Co., Ltd., Tokyo, Japan

[21] Appl. No.: 798,481

[22] Filed: Nov. 26, 1991

[30] Foreign Application Priority Data

Nov. 27, 1990 [JP] Japan ................... 2-323808

[51] Int. Cl.⁵ ............................ A47C 27/22
[52] U.S. Cl. .......................... 5/481; 5/448; 5/906; 600/9
[58] Field of Search ............ 5/448, 481, 482, 420, 5/417, 906; 600/9, 15

[56] References Cited

U.S. PATENT DOCUMENTS

| | | | |
|---|---|---|---|
| 4,330,892 | 5/1982 | Fukushima | 5/462 |
| 4,509,219 | 4/1985 | Yagi | 5/448 |
| 4,924,542 | 5/1990 | Yamaguchi | 5/481 |
| 5,035,017 | 7/1991 | Komuro | 5/448 |

FOREIGN PATENT DOCUMENTS

| | | | |
|---|---|---|---|
| 1900744 | 8/1970 | Fed. Rep. of Germany | 5/448 |
| 3522667 | 1/1987 | Fed. Rep. of Germany | 5/482 |
| 3267073 | 3/1991 | Japan | 5/906 |
| 2025234 | 1/1980 | United Kingdom | 5/448 |

Primary Examiner—Alexander Grosz
Attorney, Agent, or Firm—Browdy and Neimark

[57] ABSTRACT

A mattress for magnetic treatment which produces magnetic treatment effects by permanent magnets and chiropractic effects by protuberances while sleeping. The mattress therefore comprises an elastic body of crosslinked foamed polyethylene, foamed urethane or the like, the elastic body having protuberances on its surface for producing chiropractic effects, damper felt fixedly secured to the surface of the elastic body, the damper felt being dotted with permanent magnets, a fiber layer fixedly secure to the surface of the damper felt and used for holding the permanent magnets and the protuberances of the elastic body, and a thin soft fiber layer covering the surface of the fiber layer.

The elastic body comprises short and tall barrel-like bodies, these being disposed at fixed intervals.

6 Claims, 4 Drawing Sheets

MATTRESS FOR MAGNETIC TREATMENT

BACKGROUND OF THE INVENTION

1. Field of the Invention

The present invention relates to a mattress for magnetic treatment which produces magnetic treatment effects by permanent magnets and chiropractic or manual pressure effects by protuberances while sleeping.

2. Description of the Prior Art

Magnetism has been known to produce various magnetic treatment effects as it promotes circulation of the blood and relieves fatigue by freeing stiffness in the muscles. Varieties of products incorporating permanent magnets, such as magnetic mattresses, have also been sold. However, most of the conventional magnetic mattresses are only dotted with single permanent magnets on their surfaces (e.g., Japanese Utility Model Publication No. 6148/1989).

The conventional magnetic mattresses are often dotted with permanent magnets on their surfaces as stated above and because the magnets are widely spaced apart, the magnetic flux tends to concentrate in the vicinity of the surface of the magnetic material forming the permanent magnet. As a result, a high-density magnetic field is not readily obtainable at locations spaced some distance from the magnet and the magnet effect is barely produced deep within the human body lying on the mattress. In other words, fully satisfactory magnetic treatment effects are not to be expected from the conventional magnetic mattress.

SUMMARY OF THE INVENTION

An object of the present invention is to provide a mattress for magnetic treatment which generates magnetic lines of force that draw a high-density loop and effectively act on even a deep part of the human body, and thereby produces satisfactory magnetic treatment effects.

Another object of the present invention is to provide a mattress for magnetic treatment which produces appropriate chiropractic or manual pressure effects as well as magnetic treatment effects.

A mattress for magnetic treatment according to the present invention comprises an elastic body of crosslinked foamed polyethylene, foamed polyurethane or the like, the elastic body having protuberances on its surface for producing chiropractic or manual pressure effects, a damper or cushioning felt fixed to the surface of the elastic body, the damper felt supporting permanent magnets, a fiber layer fixed to the surface of the damper felt for holding the permanent magnets and the protuberances of the elastic body, and a thin soft fiber layer covering the surface of the fiber layer.

With this arrangement, magnetism is allowed to infiltrate deeply into the human body so as to produce satisfactory magnetic treatment effects as the permanent magnets thus disposed provide high-density magnetism of a concentrated nature over the surface of the mattress in contact with the human body.

Moreover, the protuberances provided on the elastic body produce appropriate chiropractic or manual pressure effects.

Other and further objects, features and advantages of the present invention will appear more fully from the following description.

DESCRIPTION OF THE PREFERRED EMBODIMENTS

Referring to the accompanying drawings, preferred embodiments of the present invention will be described, starting with the embodiment shown in FIGS. 1 to 4.

Figure 1:
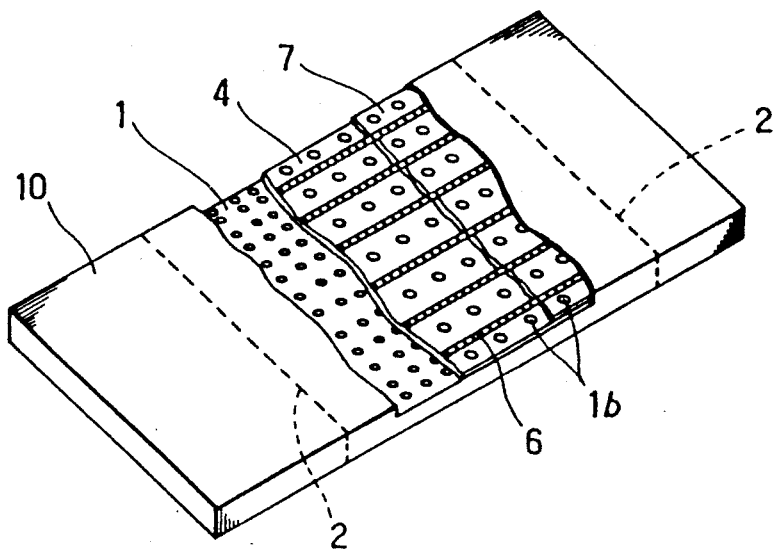
FIG. 1 is a partial cutaway perspective view of an embodiment of the present invention.
Figure 2:
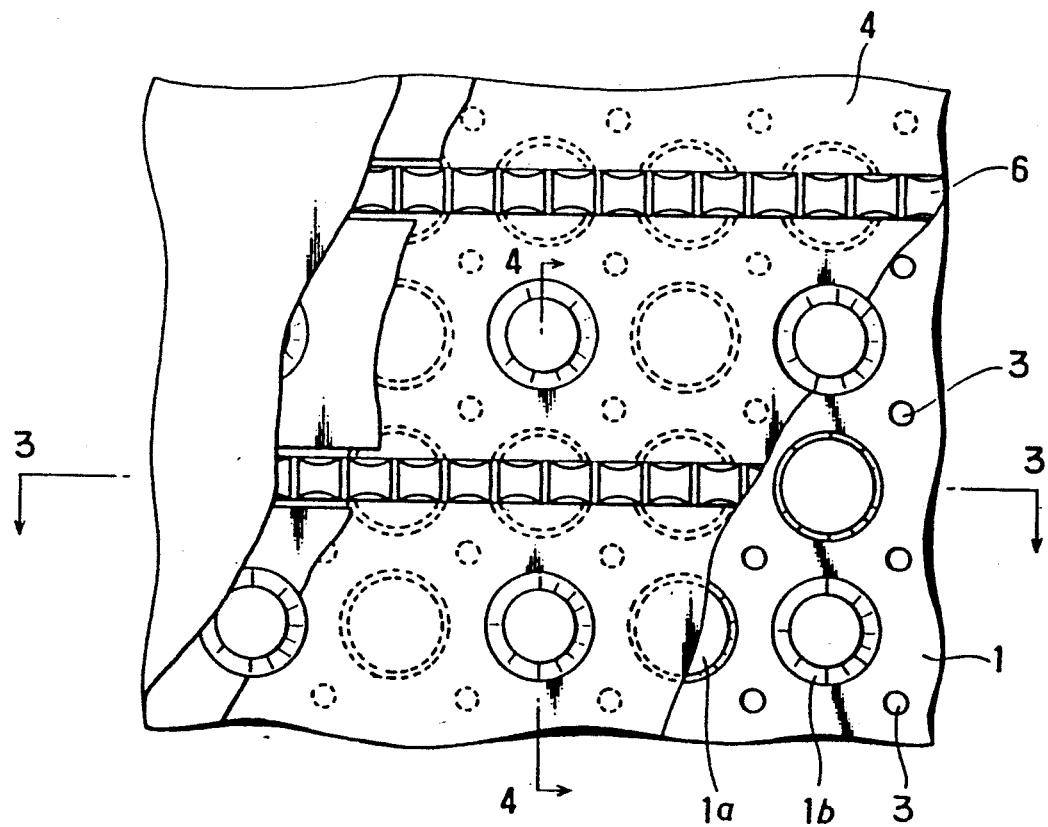
FIG. 2 is a partial enlarged top view of FIG. 1.
Figure 3:
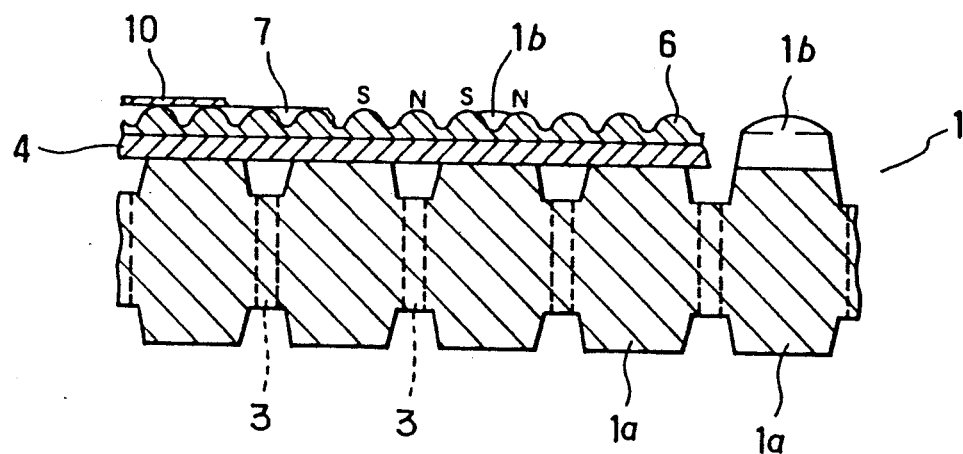
FIG. 3 is a sectional view taken on line 3—3 of FIG. 2.
Figure 4:
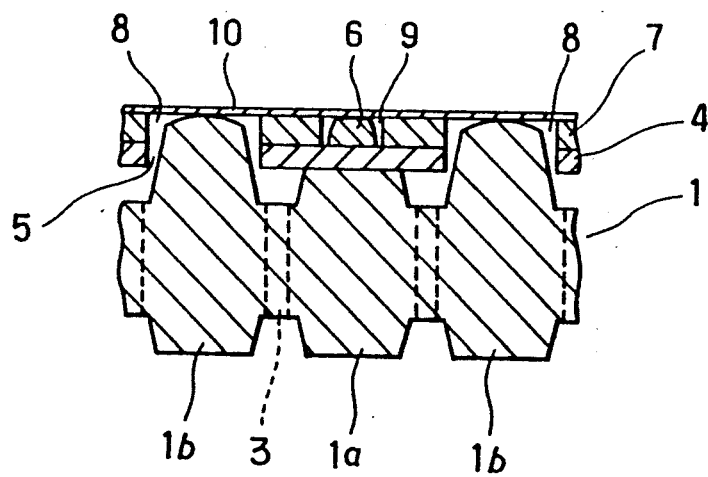
FIG. 4 is a sectional view taken on line 4—4 of FIG. 2.

FIG. 1 is a partial cutaway perspective view of the embodiment shown, wherein a turnup or fold line 2 is formed at two places (when folded in three) to make foldable a relatively thin elastic body 1 of crosslinked foamed polyethylene, foamed polyurethane or the like. The elastic body 1 is in such a form that, for instance, a number of barrel-like bodies 1a, 1b are coupled together side-by-side, with air vents 3 in the form of vertical through-holes being provided in each barrel-to-barrel coupling portion. The air vents 3 are intended to smooth or make uniform the circulation of air through the whole mattress. Among the barrel-like bodies 1a, 1b, there are a large number of short barrel-like bodies 1a and a small number of tall barrel-like bodies 1b, these being disposed at fixed intervals. In FIG. 3 at the far right there can be seen a tall barrel-like body 1b projecting upwardly behind a short barrel-like body 1a shown in cross-section.

A damper or cushioning felt 4 made of mixed-spun fibers is adhesion-bonded to the surface of the elastic body 1. Through-holes 5 (see FIG. 4) are bored in portions of the damper felt 4 corresponding to positions of the tall barrel-like bodies 1b so that the head of each tall barrel-like body 1b extends therethrough.

Several rows of continuous or strip magnetizing magnets 6 extending in the longitudinal direction of the mattress are secured to the surface of the damper felt 4 with an adhesive, for instance. The continuous magnetizing magnets 6 are formed in strip form by alternate N- and S-poles on a magnetic material mainly composed of rubber, plastics or the like and having parallel conical heads semicircular in section giving a corrugated appearance in section as shown in FIG. 3. The magnetic lines of force are generated from the continuous magnetizing magnet 6 in such a way that they are directed from the crest of the N-pole conical head to that of the adjoining S-pole conical head. As each conical head is isolated from its adjoining conical head by a valley therebetween, the magnetic path becomes long and the magnetic lines of force are generated vertically. In other words, the magnetic flux density is rendered higher at a position spaced some distance away from both magnetic poles. Therefore, the magnetic lines of force reach a deep part of the human body lying down on the present mattress, whereby satisfactory magnetic treatment effects are produced. Moreover, the conical heads produce substitute chiropractic or manual pressure effects.

The tall barrel-like bodies 1b are disposed between the parallel continuous magnetizing magnets 6. The damper felt 4 is located beneath the continuous magnetizing magnets 6 and provides support thereby preventing these magnets from sinking.

A soft fiber layer 7 (see FIG. 4) formed of synthetic fiber cotton is secured to the surface of the damper felt 4 by knitting, e.g. sewing, or bonding. The fiber layer 7 is arranged so that its top surface is at about the same height as that of the tops of the continuous magnetizing magnets 6 on the damper felt 4. Moreover, the fiber layer 7 is provided with through-holes 8 for receiving therein the heads of the respective tall barrel-like bodies 1b, each hole communicating with the through-hole 5 of the damper felt. The fiber layer 7 is also provided with longitudinal grooves 9 for receiving therein the respective continuous strip magnetizing magnets 6. Further, a thin soft fiber layer 10 made of non-woven fabric is affixed to the surface of the fiber layer 7 by sewing.

The mattress according to the present invention as described above may be covered by a sheet or a bag-like cover.

Figure 5:
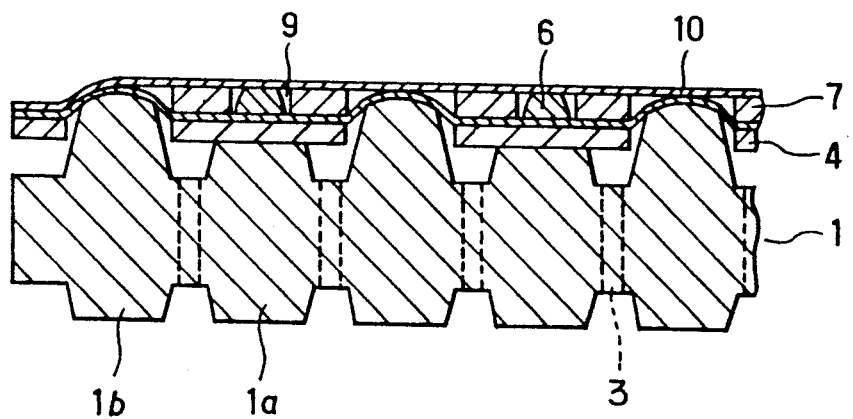
FIG. 5 is a vertical sectional view of another embodiment of the present invention.

In another embodiment as shown in FIG. 5, the thin layer 10 in the previous embodiment is formed into a bag for enclosing the continuous magnetizing magnets 6 and the fiber layer 7 and the bag 10 are affixed to the damper felt 4 by bonding or sewing.

Figure 6:
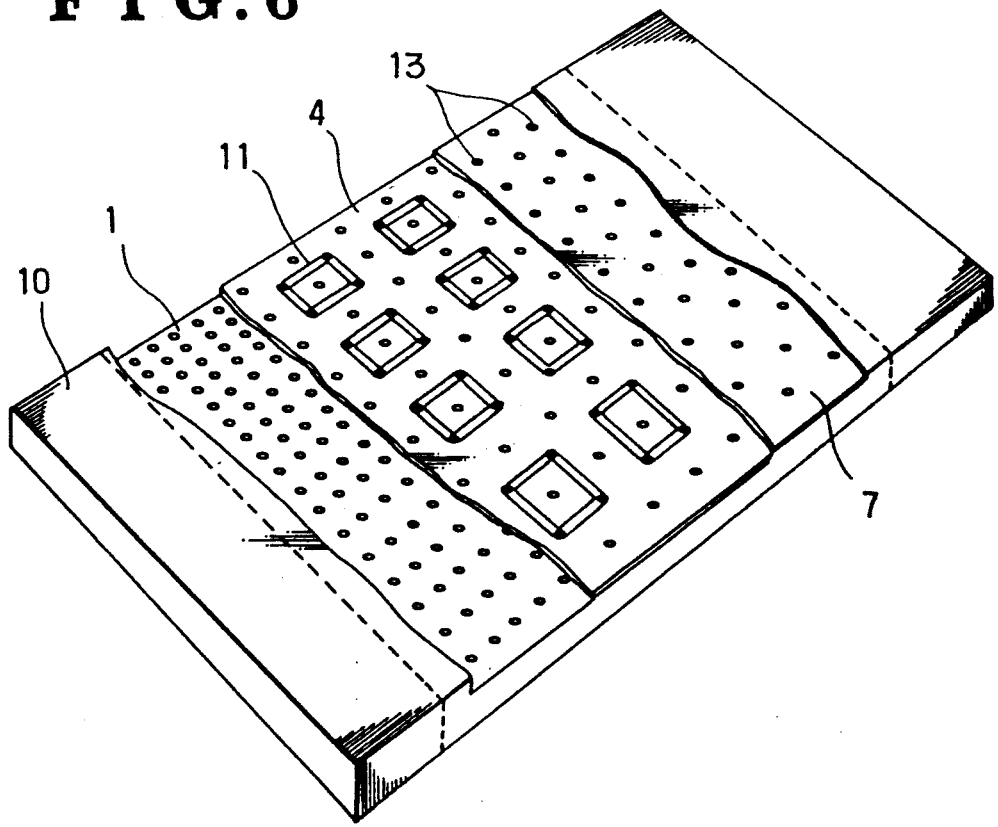
FIG. 6 is a partial cutaway perspective view of still another embodiment of the present invention.
Figure 7:
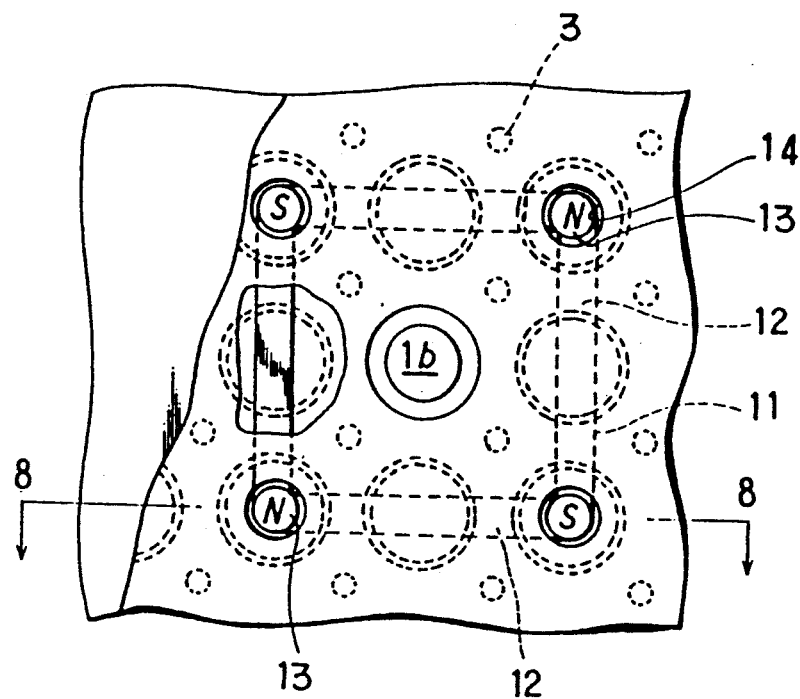
FIG. 7 is a partial enlarged top view of FIG. 6.
Figure 8:
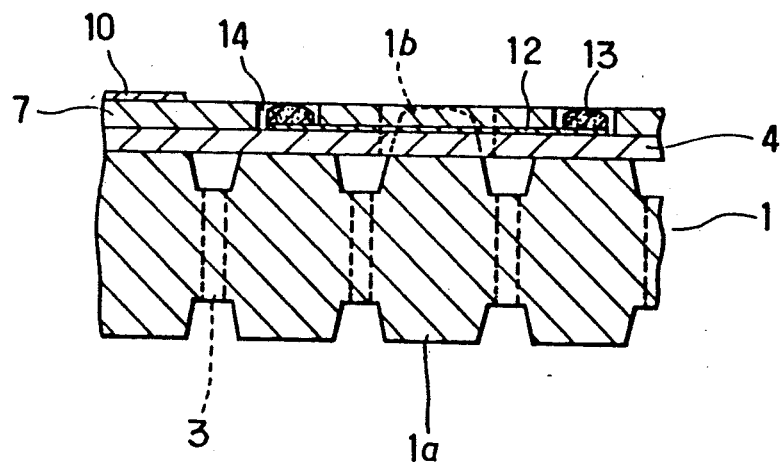
FIG. 8 is a sectional view taken on line 8—8 of FIG. 7.

FIGS. 6 to 8 inclusive refer to an embodiment wherein square multipolar magnets 11 are employed in place of the continuous magnetizing magnets 6 of the previous embodiments. The multipolar magnet 11 comprises magnetic binding plates or strips 12 disposed in the form of a square, and magnetic corner pieces 13 secured to the respective corners of the square, the magnetic corner pieces 13 adjacent to each other being oppositely polarized. The binding plates or strips 12 serve to bind together the magnetic corner pieces 13. The combination of the binding plates 12 and corner pieces 13 may be pre-formed integrally into such a square.

The multipolar magnet 11 is square in shape and one side thereof forms a double-pole magnet. As the magnetic lines of force generated from the combination of magnetic poles are caused to become concentrated, the effect thereof is enhanced. The magnetic lines of force generated from the N-seeking magnetic pole return to the S-seeking magnetic pole and proceed from the S seeking magnetic pole to the N-seeking magnetic pole through the binding plate 12. As the magnetic poles are sufficiently spaced apart, the magnetic lines of force strongly act on the human body and promote the circulation of the blood, thereby promoting treatment effect.

Even in this embodiment, the damper felt 4 is fixedly secured to the surface of the elastic body 1 and the fiber layer 7 is further secured to the surface of that combination. A through-hole 14 is formed in the fiber layer 7 (see FIG. 8) for receiving therein each magnetic strip 12 of the multipolar magnet 11 fixed onto the damper felt 4. Moreover, a shallow recess for accommodating the binding plate 12 is also formed in the fiber layer 7. The remaining part of the construction is similar to what has been described above.

As set forth above, the provision of the continuous magnetizing magnets or multipolar magnets allows high-density magnetism to infiltrate into a deep part of the human body with the effect of promoting the circulation of the blood in various parts thereof so as to relieve stiffness in the muscles. In addition to the excellent magnetic treatment effects, the elastic body equipped with the protuberances produce chiropractic or manual pressure effects appropriate to the human body, so that the mattress according to the present invention contributes to not only fatigue recovery but also maintenance of health with the treatment effects describe above.

As many apparently widely different embodiments of this invention may be made without departing from the spirit and scope thereof, it is to be understood that the invention is not limited to the specific embodiments thereof except as defined in the appended claims.

We claim:

1. In a mattress for magnetic treatment comprising an elastic body (1) of foamed elastic material, the elastic body (1) having protuberances on its surface for producing manual pressure effects, the improvement comprising a damper felt (4) fixed to the surface of the elastic body (1), the damper felt (4) supporting permanent magnets in a combined strip form (6, 11); a fiber layer (7) fixedly secured to the surface of the damper felt (4) for holding the permanent magnets (6, 11) and the protuberances of the elastic body (1); and a thin soft fiber layer (10) covering the surface of the fiber layer (7).

2. A mattress for magnetic treatment as claimed in claim 1, wherein said elastic body (1) includes short (1a) and tall (1b) barrel-like bodies joined and arranged in rows and columns, a plurality of said short barrel-like bodies (1a) being overlaid by said magnets in combined strip form (6, 11), with said tall barrel-like bodies projecting between said magnets in combined strip form.

3. A mattress for magnetic treatment as claimed in claim 2, wherein a vertical through-hole (3) is provided in a coupling portion between adjacent barrel-like bodies.

4. A mattress for magnetic treatment as claimed in claim 1, wherein said permanent magnets in combined strip form take the form of a strip (6) of magnetic material which includes parallel conical bumps each having a semicircular section, the bumps having N- and S-poles alternatively, providing a corrugated appearance in cross-section.

5. A mattress for magnetic treatment as claimed in claim 1, wherein said permanent magnets in a combined strip form take the form of multipolar magnets (11), each having a magnetic binding plate (12) in strip form defining a square, with magnet pieces (13) being arranged at all the corners, the adjacent magnet pieces having opposite poles.

6. A mattress for magnetic treatment as claimed in claim 1, wherein there is provided a thin bag-like layer for enclosing the permanent magnets and the fiber layers.

* * * * *